US006946267B2

(12) United States Patent
Liu et al.

(10) Patent No.: US 6,946,267 B2
(45) Date of Patent: Sep. 20, 2005

(54) METHOD FOR DETECTING STAPHYLOCOCCUS AUREUS

(75) Inventors: Lu-Yieng Liu, Hsinchu (TW); Jo-Yun Ho, Hsinchu (TW); Harn-Jing Terng, Hsinchu (TW)

(73) Assignee: DR. Chip Biotechnology Inc., Hsinchu (TW)

( * ) Notice: Subject to any disclaimer, the term of this patent is extended or adjusted under 35 U.S.C. 154(b) by 79 days.

(21) Appl. No.: 10/097,237

(22) Filed: Mar. 13, 2002

(65) Prior Publication Data

US 2003/0175716 A1 Sep. 18, 2003

(51) Int. Cl.[7] ........................ C12P 19/34; C07H 21/04
(52) U.S. Cl. ...................... 435/91.2; 435/6; 536/24.32; 536/24.3; 536/23.1
(58) Field of Search ............................ 536/24.32, 24.3, 536/23.1; 435/6, 91.2

(56) References Cited

U.S. PATENT DOCUMENTS

| | | | | | |
|---|---|---|---|---|---|
| 5,889,175 | A | * | 3/1999 | Mehtali et al. | 536/23.72 |
| 5,994,066 | A | * | 11/1999 | Bergeron et al. | 435/6 |
| 6,348,582 | B1 | * | 2/2002 | Black et al. | 536/23.1 |
| 2001/0053519 | A1 | * | 12/2001 | Fodor et al. | 435/6 |

FOREIGN PATENT DOCUMENTS

WO    WO 95/10614    4/1995    ........... C12N/15/55

OTHER PUBLICATIONS

Yugueros et al. (Journal of Clinical Microbiology, Dec. 2000, p. 4351–4355).*
GenBank Record AJ133520, GI: 4490611, Mar. 11, 1999.*
Sprusansky et al. (Microbiology (2001) 147:1291–1301).*
Andrew Chin. "On the Preparation and Utilization of Isolated and Purified Oligonucleotides". Katherine R. Everett Law Library, University of North Carolina at Chapel Hill. UNC Call No. QP625.O47 C45 2002, OCLC No. 49930387 (CD ROM), Mar. 14, 2002.
Christiane Cuny, et al. *Typing of Staphylococcus aureus by PCR for DNA Sequences Flanked by Transposon Tn916 Target Region and Ribosomal Binding Site*. Journal of Clinical Microbiology 34:6, Jun. 1996, p. 1502–1505.
Swee Han Goh, et al. *HSP60 Gene Sequences as Universal Targets for Microbial Species Identification: Studies with Coagulase–Negative Staphylococci*. Journal of Clinical Microbiology 34:4, Apr. 1996, p. 818–823.
Swee Han Goh, et al. *Identification of Staphylococcus Species and Subspecies by the Chaperonin 60 Gene Identification Method and Reverse Checkerboard Hybridization*. Journal of Clinical Microbiology 35:12, Dec. 1997, p. 3116–3121.

D. N. Prasanna Kumari, et al. *Comparison and Application of Ribosome Spacer DNA Amplicon Polymorphisms and Pulsed–Field Gel Electrophoresis for Differentiation of Methicillin–Resistant Staphylococcus aureus Strains*. Journal of Clinical Microbiology 35:4, Apr. 1997, p. 881–885.

Javier Yugueros Marcos, et al. *Rapid Identification and Typing of Staphylococcus aureus by PCR–Restriction Fragment Length Polymorphism Analysis and the aroA Gene*. Journal of Clinical Microbiology 37:3, Mar. 1999, p. 570–574.

Francis Martineau, et al. *Correlation between the Resistance Genotype Determined by Multiplex PCR Assays and the Antibiotic Susceptibility Patterns of Staphylococcus aureus and Staphylococcus epidermidis*. Antimicrobial Agents and Chemotherapy 44:2, Feb. 2000, p. 231–238.

Francis Martineau, et al. *Development of a Rapid PCR Assay Specific for Staphylococcus saprophyticus and Application to Direct Detection from Urine Samples*. Journal of Clinical Microbiology 38:9, Sep. 2000, p. 3280–3284.

Francis Martineau, et al. *Species–Specific and Ubiquitous–DNA–Based Assays for Rapid Identification of Staphylococcus aureus*. Journal of Clinical Microbiology 36:3, Mar. 1998, p. 618–623.

Francis Martineau, et al. *Species–Specific and Ubiquitous–DNA–Based Assays for Rapid Identification of Staphylococcus epidermidis*. Journal of Clinical Microbiology 34:12, Dec. 1996, p. 2888–2893.

* cited by examiner

Primary Examiner—Juliet C. Switzer
(74) Attorney, Agent, or Firm—Fish & Richardson P.C.

(57) ABSTRACT

Specific nucleic acid sequences, e.g., SEQ ID NOs:2–8, for detecting *Staphylococcus aureus*. Also disclosed is a method of detecting *Staphylococcus aureus*. The method includes providing a sample having a nucleic acid from an unknown microorganism; amplifying the nucleic acid with a pair of primers, each containing an oligo-nucleotide selected from the *Staphylococcus aureus* gap regulator gene region (SEQ ID NO:1) and each having 14–40 nucleotides in length; and detecting an amplification product. Detection of the amplification product, e.g., using SEQ ID NO:2, 7, or 8 as a probe, indicates the presence of *Staphylococcus aureus*.

15 Claims, No Drawings

SEQUENCE LISTING

<160> NUMBER OF SEQ ID NOS: 9

<210> SEQ ID NO 1
<211> LENGTH: 1792
<212> TYPE: DNA
<213> ORGANISM: Staphylococcus aureus
<220> FEATURE:
<221> NAME/KEY: CDS
<222> LOCATION: (779)...(1789)

<400> SEQUENCE: 1

```
caaaataatg ctaatgataa gtagtattta gtcaaacaaa aatgaaccag tatgacagac      60
aacacaatta attaggttgt ctcgaatatt ggttcttatt tttataattg ttaattaggg     120
gagagatgat acttaaatag ttagttgttt gttttgcgga tagtgaaatt tattttgagt     180
gaggtgggac agaaatgata ttttcgcaaa atttatttcg tcgtccaacc ccaactccca     240
ttgcctgtag aaattgggag gagccaatct atgttggggc cccgccaact tgcattgtct     300
gtagaaattg ggaatccaat ttctctatgt tggggcccat ccccaacttc ccattgtctg     360
tacaaattgg gaatccaatt tcactatgtt ggggcccctg actttaattg gaaaagcttg     420
ttacaagcga aattttgttc agtcaattac tactaatgta aattttcggg ttctagagca     480
ttgatttatg tcctagtctc aaataataag caaatgatta gcgagttgtt ataagggtat     540
```

-continued

```
acatttgact acagcgaata aaataaaacg ttttgttgta taacaaatcg aaaatatatt    600
gcaagcgctt tatcaaatta tttagaaaat ttaagtttta tgcttgcaat ttttgaaata    660
gaatagtact attgcaagtg taaagaggtt aattttttgtc ccacgcggga cttaaaaagg   720
caaccactgg ttgtgatata tccttattta catttataaa tataaggagg aggtagta     778
```

| | | | | | | | | | | | | | | | | |
|---|---|---|---|---|---|---|---|---|---|---|---|---|---|---|---|---|
| gtg | aaa | gac | tta | ttg | caa | gca | cag | caa | aag | ctt | ata | ccg | gat | ctc | ata | 826 |
| Val | Lys | Asp | Leu | Leu | Gln | Ala | Gln | Gln | Lys | Leu | Ile | Pro | Asp | Leu | Ile | |
| 1 | | | | 5 | | | | | 10 | | | | | 15 | | |
| gat | aaa | atg | tat | aaa | cgt | ttt | tct | att | ctt | act | act | atc | tca | aaa | aat | 874 |
| Asp | Lys | Met | Tyr | Lys | Arg | Phe | Ser | Ile | Leu | Thr | Thr | Ile | Ser | Lys | Asn | |
| | | | 20 | | | | | 25 | | | | | 30 | | | |
| cag | cct | gtc | gga | cgt | cga | agt | tta | agc | gaa | cat | atg | gat | atg | act | gaa | 922 |
| Gln | Pro | Val | Gly | Arg | Arg | Ser | Leu | Ser | Glu | His | Met | Asp | Met | Thr | Glu | |
| | | | | 35 | | | | | 40 | | | | | 45 | | |
| cgt | gta | ctg | cgt | tct | gaa | aca | gat | atg | ctt | aag | aaa | caa | gat | ttg | ata | 970 |
| Arg | Val | Leu | Arg | Ser | Glu | Thr | Asp | Met | Leu | Lys | Lys | Gln | Asp | Leu | Ile | |
| | | 50 | | | | | 55 | | | | | 60 | | | | |
| aaa | gtt | aag | cct | acc | ggt | atg | gaa | att | aca | gct | gaa | ggt | gag | caa | ctg | 1018 |
| Lys | Val | Lys | Pro | Thr | Gly | Met | Glu | Ile | Thr | Ala | Glu | Gly | Glu | Gln | Leu | |
| 65 | | | | | 70 | | | | | 75 | | | | | 80 | |
| att | tcg | caa | ttg | aaa | ggt | tac | ttt | gat | atc | tat | gca | gat | gac | aat | cgt | 1066 |
| Ile | Ser | Gln | Leu | Lys | Gly | Tyr | Phe | Asp | Ile | Tyr | Ala | Asp | Asp | Asn | Arg | |
| | | | | 85 | | | | | 90 | | | | | 95 | | |
| ctg | tca | gaa | ggt | att | aag | aat | aaa | ttt | caa | att | aag | gaa | gtt | cat | gtt | 1114 |
| Leu | Ser | Glu | Gly | Ile | Lys | Asn | Lys | Phe | Gln | Ile | Lys | Glu | Val | His | Val | |
| | | | | 100 | | | | | 105 | | | | | 110 | | |
| gtt | cct | ggt | gat | gct | gat | aat | agc | caa | tct | gtt | aaa | aca | gaa | tta | ggt | 1162 |
| Val | Pro | Gly | Asp | Ala | Asp | Asn | Ser | Gln | Ser | Val | Lys | Thr | Glu | Leu | Gly | |
| | | | 115 | | | | | 120 | | | | | 125 | | | |
| aga | caa | gca | ggt | caa | tta | ctt | gaa | ggc | ata | tta | caa | gaa | gat | gcg | ata | 1210 |
| Arg | Gln | Ala | Gly | Gln | Leu | Leu | Glu | Gly | Ile | Leu | Gln | Glu | Asp | Ala | Ile | |
| | | 130 | | | | | 135 | | | | | 140 | | | | |
| gtt | gct | gta | act | ggc | gga | tcc | acg | atg | gca | tgt | gtt | agt | gaa | gca | att | 1258 |
| Val | Ala | Val | Thr | Gly | Gly | Ser | Thr | Met | Ala | Cys | Val | Ser | Glu | Ala | Ile | |
| 145 | | | | | 150 | | | | | 155 | | | | | 160 | |
| cat | tta | tta | cca | tat | aat | gta | ttc | ttc | gta | cca | gcc | aga | ggt | gga | cta | 1306 |
| His | Leu | Leu | Pro | Tyr | Asn | Val | Phe | Phe | Val | Pro | Ala | Arg | Gly | Gly | Leu | |
| | | | | 165 | | | | | 170 | | | | | 175 | | |
| ggc | gaa | aat | gtt | gtc | ttt | cag | gca | aac | aca | att | gca | gct | agt | atg | gca | 1354 |
| Gly | Glu | Asn | Val | Val | Phe | Gln | Ala | Asn | Thr | Ile | Ala | Ala | Ser | Met | Ala | |
| | | | | 180 | | | | | 185 | | | | | 190 | | |
| caa | caa | gct | ggc | ggt | tat | tat | acg | acg | atg | tat | gta | cct | gat | aat | gtc | 1402 |
| Gln | Gln | Ala | Gly | Gly | Tyr | Tyr | Thr | Thr | Met | Tyr | Val | Pro | Asp | Asn | Val | |
| | | | | 195 | | | | | 200 | | | | | 205 | | |
| agc | gaa | aca | aca | tat | aac | aca | ttg | ttg | tta | gag | cca | tca | gtc | ata | aac | 1450 |
| Ser | Glu | Thr | Thr | Tyr | Asn | Thr | Leu | Leu | Leu | Glu | Pro | Ser | Val | Ile | Asn | |
| | | | 210 | | | | | 215 | | | | | 220 | | | |
| act | tta | gac | aaa | att | aaa | caa | gca | aac | gtt | ata | tta | cac | ggc | att | ggt | 1498 |
| Thr | Leu | Asp | Lys | Ile | Lys | Gln | Ala | Asn | Val | Ile | Leu | His | Gly | Ile | Gly | |
| 225 | | | | | 230 | | | | | 235 | | | | | 240 | |
| gat | gcg | ctg | aag | atg | gcg | cat | cga | cgt | caa | tca | cct | gaa | aag | gtc | att | 1546 |
| Asp | Ala | Leu | Lys | Met | Ala | His | Arg | Arg | Gln | Ser | Pro | Glu | Lys | Val | Ile | |
| | | | | 245 | | | | | 250 | | | | | 255 | | |
| gaa | caa | ctt | caa | cat | cat | caa | gct | gtc | gga | gag | gca | ttt | ggt | tat | tat | 1594 |
| Glu | Gln | Leu | Gln | His | His | Gln | Ala | Val | Gly | Glu | Ala | Phe | Gly | Tyr | Tyr | |
| | | | | 260 | | | | | 265 | | | | | 270 | | |
| ttt | gat | aca | caa | ggt | caa | att | gtc | cat | aag | gtt | aaa | aca | att | gga | ctt | 1642 |
| Phe | Asp | Thr | Gln | Gly | Gln | Ile | Val | His | Lys | Val | Lys | Thr | Ile | Gly | Leu | |

```
            275                 280                 285
caa tta gaa gac ctt gaa tca aaa gac ttt att ttt gca gtt gca gga    1690
Gln Leu Glu Asp Leu Glu Ser Lys Asp Phe Ile Phe Ala Val Ala Gly
        290                 295                 300 ggc aaa tcg aaa ggt gaa gca att aaa gca tac ttg acg att gca ccc    1738
Gly Lys Ser Lys Gly Glu Ala Ile Lys Ala Tyr Leu Thr Ile Ala Pro
305                 310                 315                 320 aag aat aca gtg tta atc act gat gaa gcc gca gca aag ata ata ctt    1786
Lys Asn Thr Val Leu Ile Thr Asp Glu Ala Ala Ala Lys Ile Ile Leu
                325                 330                 335 gaa taa                                                            1792
Glu

<210> SEQ ID NO 2
<211> LENGTH: 1260
<212> TYPE: DNA
<213> ORGANISM: Staphylococcus aureus

<400> SEQUENCE: 2
caaaataatg ctaatgataa gtagtattta gtcaaacaaa aatgaaccag tatgacagac      60
aacacaatta attaggttgt ctcgaatatt ggttcttatt tttataattg ttaattaggg     120
gagagatgat acttaaatag ttagttgttt gttttgcgga tagtgaaatt tattttgagt     180
gaggtgggac agaaatgata ttttcgcaaa atttatttcg tcgtccaacc ccaactccca     240
ttgcctgtag aaattgggag gagccaatct atgttgggc cccgccaact tgcattgtct      300
gtagaaattg ggaatccaat ttctctatgt tggggcccat ccccaacttc ccattgtctg    360
tacaaattgg gaatccaatt tcactatgtt ggggcccctg actttaattg gaaaagcttg    420
ttacaagcga attttgttc agtcaattac tactaatgta aattttcggg ttctagagca     480
ttgatttatg tcctagtctc aaataataag caaatgatta gcgagttgtt ataagggtat    540
acatttgact acagcgaata aaataaaacg ttttgttgta taacaaatcg aaaatatatt    600
gcaagcgctt tatcaaatta tttagaaaat ttaagttta tgcttgcaat ttttgaaata     660
gaatagtact attgcaagtg taagagggtt aattttgtc ccacgcggga cttaaaaagg     720
caaccactgg ttgtgatata tccttattta catttataaa tataaggagg aggtagtagt    780
gaaagactta ttgcaagcac agcaaaagct tataccggat ctcatagata aaatgtataa    840 acgttttct attcttacta ctatctcaaa aaatcagcct gtcggacgtc gaagtttaag     900
cgaacatatg gatatgactg aacgtgtact gcgttctgaa acagatatgc ttaagaaaca    960
agatttgata aagtaagc ctaccggtat ggaaattaca gctgaaggtg agcaactgat     1020
ttcgcaattg aaaggttact ttgatatcta tgcagatgac aatcgtctgt cagaaggtat   1080
taagaataaa tttcaaatta aggaagttca tgttgttcct ggtgatgctg ataatagcca   1140
atctgttaaa acagaattag gtagacaagc aggtcaatta cttgaaggca tattacaaga   1200
agatgcgata gttgctgtaa ctggcggatc cacgatggca tgtgttagtg aagcaattca   1260

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ggtgatgctg ataatagcca                                                 20
```

-continued

```
<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
tataataacc gccagcttgt tg                                              22

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cggtatggaa attacagctg                                                 20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
taggcgaaaa tgttgtcttt                                                 20

<210> SEQ ID NO 7
<211> LENGTH: 256
<212> TYPE: DNA
<213> ORGANISM: Staphylococcus aureus

<400> SEQUENCE: 7
ggtgatgctg ataatagcca atctgttaaa acagaattag gtagacaagc aggtcaatta     60
cttgaaggca tattcaaga agatgcgata gttgctgtaa ctggcggatc cacgatggca    120
tgtgttagtg aagcaattca tttattacca tataatgtat tcttcgtacc agccagaggt   180
ggactaggcg aaaatgttgt ctttcaggca aacacaattg cagctagtat ggcacaacaa   240
gctggcggtt attata                                                   256

<210> SEQ ID NO 8
<211> LENGTH: 340
<212> TYPE: DNA
<213> ORGANISM: Staphylococcus aureus

<400> SEQUENCE: 8
cggtatggaa attacagctg aaggtgagca actgatttcg caattgaaag gttactttga     60
tatctatgca gatgacaatc gtctgtcaga aggtattaag aataaatttc aaattaagga   120
agttcatgtt gttcctggtg atgctgataa tagccaatct gttaaaacag aattaggtag   180
acaagcaggt caattacttg aaggcatatt caagaagat gcgatagttg ctgtaactgg    240
cggatccacg atggcatgtg ttagtgaagc aattcattta ttaccatata atgtattctt   300
cgtaccagcc agaggtggac taggcgaaaa tgttgtcttt                         340

<210> SEQ ID NO 9
<211> LENGTH: 337
<212> TYPE: PRT
<213> ORGANISM: Staphylococcus aureus
```

-continued

<400> SEQUENCE: 9

Val Lys Asp Leu Leu Gln Ala Gln Gln Lys Leu Ile Pro Asp Leu Ile
 1               5                  10                  15

Asp Lys Met Tyr Lys Arg Phe Ser Ile Leu Thr Thr Ile Ser Lys Asn
            20                  25                  30

Gln Pro Val Gly Arg Arg Ser Leu Ser Glu His Met Asp Met Thr Glu
        35                  40                  45

Arg Val Leu Arg Ser Glu Thr Asp Met Leu Lys Lys Gln Asp Leu Ile
    50                  55                  60

Lys Val Lys Pro Thr Gly Met Glu Ile Thr Ala Glu Gly Glu Gln Leu
65                  70                  75                  80

Ile Ser Gln Leu Lys Gly Tyr Phe Asp Ile Tyr Ala Asp Asp Asn Arg
                85                  90                  95

Leu Ser Glu Gly Ile Lys Asn Lys Phe Gln Ile Lys Glu Val His Val
            100                 105                 110

Val Pro Gly Asp Ala Asp Asn Ser Gln Ser Val Lys Thr Glu Leu Gly
        115                 120                 125

Arg Gln Ala Gly Gln Leu Leu Glu Gly Ile Leu Gln Glu Asp Ala Ile
    130                 135                 140

Val Ala Val Thr Gly Gly Ser Thr Met Ala Cys Val Ser Glu Ala Ile
145                 150                 155                 160

His Leu Leu Pro Tyr Asn Val Phe Phe Val Pro Ala Arg Gly Gly Leu
                165                 170                 175

Gly Glu Asn Val Val Phe Gln Ala Asn Thr Ile Ala Ala Ser Met Ala
            180                 185                 190

Gln Gln Ala Gly Gly Tyr Tyr Thr Thr Met Tyr Val Pro Asp Asn Val
        195                 200                 205

Ser Glu Thr Thr Tyr Asn Thr Leu Leu Glu Pro Ser Val Ile Asn
        210                 215                 220

Thr Leu Asp Lys Ile Lys Gln Ala Asn Val Ile Leu His Gly Ile Gly
225                 230                 235                 240

Asp Ala Leu Lys Met Ala His Arg Arg Gln Ser Pro Glu Lys Val Ile
                245                 250                 255

Glu Gln Leu Gln His His Gln Ala Val Gly Glu Ala Phe Gly Tyr Tyr
            260                 265                 270

Phe Asp Thr Gln Gly Gln Ile Val His Lys Val Lys Thr Ile Gly Leu
        275                 280                 285

Gln Leu Glu Asp Leu Glu Ser Lys Asp Phe Ile Phe Ala Val Ala Gly
    290                 295                 300

Gly Lys Ser Lys Gly Glu Ala Ile Lys Ala Tyr Leu Thr Ile Ala Pro
305                 310                 315                 320

Lys Asn Thr Val Leu Ile Thr Asp Glu Ala Ala Lys Ile Ile Leu
                325                 330                 335

Glu

METHOD FOR DETECTING STAPHYLOCOCCUS AUREUS

BACKGROUND

Traditional methods of detecting microorganisms rely on time-consuming growth in culture media, followed by isolation and biochemical or serological identification. The entire process usually takes 24–48 hours. Many methods for rapid detection of microorganisms have recently been developed, including miniaturized biochemical analyses, antibody- and DNA-based tests, and modified conventional assays.

Staphylococcus aureus has been identified as the causative agent in many food poisoning outbreaks (Bennet and Lancette (2001) Bacteriological Analytical Manual Online, Chapter 12 Staphylococcus aureus; U.S. Food & Drug Administration, Center for Food Safety and Applied Nutrition; www.cfsan.fda.gov/~bam/bam-12.html). It is also one of the major pathogens responsible for many opportunistic infections in humans and animals (Kloos and Bannerman (1995) Staphylococcus and Micrococcus, p. 282–298. In Murray et al. (ed.), Manual of Clinical Microbiology, 6$^{th}$ ed. American Society for Microbiology, Wasgington, D.C.). Rapid and accurate detection of Staphylococcus aureus is important for preventing food poisoning outbreaks, and for diagnosis and treatment of Staphylococcus aureus infections.

SUMMARY

The present invention relates to specific nucleic acid sequences selected from the Staphylococcus aureus gap regulator gene region for detecting Staphylococcus aureus.

The Staphylococcus aureus gap regulator gene region, i.e., nucleotides 1–1792 of GenBank Accession Number AJ133520 (SEQ ID NO:1) is shown below:

1 CAAAATAATG CTAATGATAA GTAGTATTTA GTCAAACAAA AATGAACCAG
51 TATGACAGAC AACACAATTA ATTAGGTTGT CTC-GAATATT GGTTCTTATT
101 TTTATAATTG TTAATTAGGG GAGAGATGAT ACT-TAAATAG TTAGTTGTTT
151 GTTTTGCGGA TAGTGAAATT TATTTTGAGT GAGGTGGGAC AGAAATGATA
201 TTTTCGCAAA ATTTATTTCG TCGTCCAACC CCAACTCCCA TTGCCTGTAG
251 AAATTGGGAG GAGCCAATCT ATGTTGGGGC CCCGCCAACT TGCATTGTCT
301 GTAGAAATTG GGAATCCAAT TTCTCTATGT TGGGGCCCAT CCCCAACTTC
351 CCATTGTCTG TACAAATTGG GAATCCAATT TCACTATGTT GGGGCCCCTG
401 ACTTTAATTG GAAAAGCTTG TTACAAGCGA AATTTTGTTC AGTCAATTAC
451 TACTAATGTA AATTTTCGGG TTCTAGAGCA TTGATTTATG TCCTAGTCTC
501 AAATAATAAG CAAATGATTA GCGAGTTGTT ATAAGGGTAT ACATTTGACT
551 ACAGCGAATA AAATAAAACG TTTTGTTGTA TAACAAATCG AAAATATATT
601 GCAAGCGCTT TATCAAATTA TTTAGAAAAT TTAAGTTTTA TGCTTGCAAT
651 TTTTGAAATA GAATAGTACT ATTGCAAGTG TAAAGAGGTT AATTTTTGTC
701 CCACGCGGGA CTTAAAAAGG CAACCACTGG TTGTGATATA TCCTTATTTA
751 CATTTATAAA TATAAGGAGG AGGTAGTAGT GAAAGACTTA TTGCAAGCAC
801 AGCAAAAGCT TATACCGGAT CTCATAGATA AAATGTATAA ACGTTTTTCT
851 ATTCTTACTA CTATCTCAAA AAATCAGCCT GTCGGACGTC GAAGTTTAAG
901 CGAACATATG GATATGACTG AACGTGTACT GCGTTCTGAA ACAGATATGC
951 TTAAGAAACA AGATTTGATA AAAGTTAAGC CTACCGGTAT GGAAATTACA
1001 GCTGAAGGTG AGCAACTGAT TTCGCAATTG AAAGGTTACT TTGATATCTA
1051 TGCAGATGAC AATCGTCTGT CAGAAGGTAT TAAGAATAAA TTTCAAATTA
1101 AGGAAGTTCA TGTTGTTCCT GGTGATGCTG ATAATAGCCA ATCTGTTAAA
1151 ACAGAATTAG GTAGACAAGC AGGTCAATTA CTTGAAGGCA TATTACAAGA
1201 AGATGCGATA GTTGCTGTAA CTGGCGGATC CACGATGGCA TGTGTTAGTG
1251 AAGCAATTCA TTTATTACCA TATAATGTAT TCT-TCGTACC AGCCAGAGGT
1301 GGACTAGGCG AAAATGTTGT CTTTCAGGCA AACACAATTG CAGCTAGTAT
1351 GGCACAACAA GCTGGCGGTT ATTATACGAC GATGTATGTA CCTGATAATG
1401 TCAGCGAAAC AACATATAAC ACATTGTTGT TAGAGCCATC AGTCATAAAC
1451 ACTTTAGACA AAATTAAACA AGCAAACGTT ATATTACACG GCATTGGTGA
1501 TGCGCTGAAG ATGGCGCATC GACGTCAATC ACCTGAAAAG GTCATTGAAC
1551 AACTTCAACA TCATCAAGCT GTCGGAGAGG CATTTGGTTA TTATTTTGAT
1601 ACACAAGGTC AAATTGTCCA TAAGGTTAAA ACAATTGGAC TTCAATTAGA
1651 AGACCTTGAA TCAAAAGACT TTATTTTTGC AGTTGCAGGA GGCAAATCGA
1701 AAGGTGAAGC AATTAAAGCA TACTTGACGA TTGCACCCAA GAATACAGTG
1751 TTAATCACTG ATGAAGCCGC AGCAAAGATA ATACTTGAAT AA (SEQ ID NO:1)

In one aspect, this invention features a pair of amplification primers, each containing an oligo-nucleotide selected from the Staphylococcus aureus gap regulator gene region (e.g., one selected from nucleotides 1–1260 shown above (SEQ ID NO:2) and the other selected from the complement of SEQ ID NO:2), wherein each primer has 14–40 (e.g., 14–30 and 14–20) nucleotides in length. These amplification primers can be used for detecting Staphylococcus aureus. One example of such a primer pair is SEQ ID NO:3 (nucleotides 1121–1140 shown above) and SEQ ID NO:4 (the complement of nucleotides 1376–1355 shown above). Another example is SEQ ID NO:5 (nucleotides 985–1004 shown above) and SEQ ID NO:6 (the complement of nucleotides 1324–1305 shown above).

In another aspect, this invention features a nucleic acid obtained from amplification of an Staphylococcus aureus nucleic acid template with a pair of primers, each containing, respectively, SEQ ID NOs:3 and 4, or SEQ ID NOs:5 and 6, and each having 20–40 (e.g., 20–30) nucleotides in length. The amplification product can be used as a hybridization probe for Staphylococcus aureus detection. In one example, the upstream primer is SEQ ID NO:3 and the downstream primer is SEQ ID NO:4. In another example, the upstream primer is SEQ ID NO:5 and the downstream primer is SEQ ID NO:6.

In yet another aspect, this invention features a nucleic acid that is 10–1000 (e.g., 10–500, 10–250, or 10–50) nucleotides in length and contains an oligo-nucleotide selected from the *Staphylococcus aureus* gap regulator gene region. For example, the oligo-nucleotide can be SEQ ID NO:2 or its complement, SEQ ID NO:7 (nucleotides 1121–1376 shown above) or its complement, SEQ ID NO:8 (nucleotides 985–1324 shown above) or its complement; or a fragment selected from SEQ ID NO:2, 7, or 8, or its complement. These nucleic acids can be used as hybridization probes for detecting *Staphylococcus aureus*.

Also within the scope of this invention is a method of detecting *Staphylococcus aureus* using two or more of the nucleic acids described above. The method includes (1) providing a sample having a nucleic acid from an unknown microorganism; (2) amplifying the nucleic acid with a pair of primers, each containing an oligo-nucleotide selected from the *Staphylococcus aureus* gap regulator gene region (e.g., SEQ ID NO:2 and its complement), and each having 14–40 (e.g., 14–30 and 14–20) nucleotides in length; and (3) detecting an amplification product. If the size of the detected amplification product is as predicted according to the locations of the primers, the presence of *Staphylococcus aureus* is indicated. The pair of primers can be, for example, SEQ ID NOs:3 and 4, or SEQ ID NOs:5 and 6. The detecting step can include hybridizing the amplification product to a nucleic acid that is 10–1000 (e.g., 10–500, 10–250, or 10–50) nucleotides in length and contains an oligo-nucleotide selected from the *Staphylococcus aureus* gap regulator gene region. For example, the oligo-nucleotide can be SEQ ID NO:2 or its complement, SEQ ID NO:7 or its complement, SEQ ID NO:8 or its complement; or a fragment selected from SEQ ID NO:2, 7, or 8, or its complement.

Further within the scope of this invention is a kit for detecting *Staphylococcus aureus*. The kit contains one or more of the nucleic acids described above (e.g., SEQ ID NOs:3 and 4 as a primer pair and SEQ ID NO:7 as a probe). It may include other components such as a DNA polymerase, a PCR buffer, or a solid support on which one or more of the above-described probes are immobilized.

The present invention provides a fast, accurate, and sensitive method for *Staphylococcus aureus* detection. The details of one or more embodiments of the invention are set forth in the accompanying description below. Other advantages, features, and objects of the invention will be apparent from the detailed description, and from the claims.

DETAILED DESCRIPTION

The present invention relates to a method for detecting *Staphylococcus aureus*. Specifically, a nucleic acid template from a sample suspected of containing *Staphylococcus aureus* is amplified with a pair of *Staphylococcus aureus*-specific primers. The amplification product, if any, is detected by either gel electrophoresis and staining, or by probe hybridization. If the size of the detected amplification product is as predicted according to the locations of the primers, the presence of *Staphylococcus aureus* in the sample is indicated.

The nucleic acid template can be DNA (e.g., a genomic fragment or a restriction fragment) or RNA, in a purified or unpurified form. A nucleic acid template can be obtained from a water sample or a food sample. It can also be obtained from a biological sample (e.g., a specimen from a patient or an animal).

The present invention features *Staphylococcus aureus*-specific primers selected from the gap regulator gene region, i.e., nucleotides 1–1792 of GenBank Accession Number AJ133520 (SEQ ID NO:1). This region contains an open reading frame, i.e., nucleotides 779–1792 shown above (SEQ ID NO:9) encoding a glycolytic operon regulator protein with 337 amino acids. Specifically, GenBank BLAST search results indicate that DNA sequence of SEQ ID NO:2 (nucleotides 1–1260 shown above) is specific for *Staphylococcus aureus*. A pair of amplification primers can be selected from SEQ ID NO:2 and its complement for detecting *Staphylococcus aureus*.

In one of the selected primer pairs, the forward primer is a 20 oligo-nucleotide Sta27, 5'-GGTGATGCTGATAATAGCCA-3' (SEQ ID NO:3), and the reverse primer is a 22 oligo-nucleotide Sta28, 5'-TATAATAACCGCCAGCTTGTTG-3' (SEQ ID NO:4).

In another selected primer pair, the forward primer is a 20 oligo-nucleotide Sta29, 5'-CGGTATGGAAATTACAGCTG-3' (SEQ ID NO:5), and the reverse primer is another 20 oligo-nucleotide Sta30, 5'-TAGGCGAAAATGTTGTCTTT-3' (SEQ ID NO:6).

Typically, a primer is 14–40 nucleotides in length. See PCR Application Manual, Boehringer Mannheim, 1995, page 37. In this invention, a pair of primers, each containing an oligo-nucleotide selected from the *Staphylococcus aureus* gap regulator gene region (e.g., SEQ ID NOs:3–6) and having 14–40 (e.g., 14–30 and 14–20) nucleotides in length, can be used to amplify a *Staphylococcus aureus* template. *Staphylococcus aureus* sequences can be added to either the 5'-end or the 3'-end of the selected oligo-nucleotides; non-*Staphylococcus aureus* sequences can be added to the 5'-end of the selected oligo-nucleotides. An example of a non-*Staphylococcus aureus* sequence is a sequence containing a restriction site, which can be used to facilitate cloning of the amplification product.

The present invention also features *Staphylococcus aureus*-specific probes chosen from the *Staphylococcus aureus* gap regulator gene region, e.g., SEQ ID NO:2 or its complement, SEQ ID NO:7 (i.e., a DNA sequence between and incuding primers Sta27 and Sta28 described above) or its complement, SEQ ID NO:8 (i.e., a DNA sequence between and including primers Sta29 and Sta30 described above) or its complement. GanBank BLAST search results indicate that the nucleic acid sequences amplified with primer pair Sta27 and Sta28 and primer pair Sta29 and Sta30 are both *Staphylococcus aureus*-specific. These probes can be used for detecting *Staphylococcus aureus* by hybridizing to an unamplified *Staphylococcus aureus* nucleic acid or a *Staphylococcus aureus* nucleic acid amplified with the above-described primer pairs. Typically, a probe has 10–1000 (e.g., 10–500, 10–250, or 10–50) nucleotides in length. The probes can be simply SEQ ID NO:2, SEQ ID NO:7, SEQ ID NO:8, and their complementary sequences.

The probes can be immobilized on the surface of a solid support, such as a membrane (a nylon-membrane or a nitrocellulose membrane), a glass, or a plastic polymer. Immobilization of probes to a membrane can be achieved by baking at 80° C. or UV cross-linking. The probes can also be covalently linked to a material (e.g., poly-lysine) coated on the surface of a glass. In addition, a novel method of immobilizing probes on a plastic polymer has recently been developed. See U.S. application Ser. No. 09/906,207. Alternatively, the probes can be synthesized de novo at precise positions on a solid substrate. See Schena et al., 1995, *Science* 270: 467; Kozal et al., 1996, *Nature Medicine* 2(7): 753; Cheng et al., 1996, *Nucleic Acids Res.* 24(2): 380; Lipshutz et al., 1995, *BioTechniques* 19(3): 442; Pease et al., 1994, Proc. Natl. Acad. Sci. USA 91: 5022; Fodor et al., 1993, Nature 364: 555; and Fodor et al., WO 92/10092.

A target DNA sequence (i.e., an unamplified *Staphylococcus aureus* nucleic acid or a *Staphylococcus aureus* nucleic acid amplified with the above-described primer pairs) can be detected by binding it to an immobilized probe. To facilitate the detection, a labeled amplification product can be generated with a labeled amplification primer. Alternatively, the labeling can be done, chemically or enzymatically, after amplification. Examples of labeling reagents include, but are not limited to, a fluorescent molecule (e.g., fluorescein and rhodamine), a radioactive isotope (e.g., $^{32}P$ and $^{125}I$), a colorimetric reagent, and a chemiluminescent reagent. Biotin and digoxgenin are frequently used for colorimetric detection on a membrane or a plastic polymer. Fluorescent labels, such as Cy3 and Cy5, are widely used for detection on a glass. In addition, artificial tagging tails (e.g., a protein or its antibody) can be conjugated to the 5'-end of the primers or either end of the probes. See Stetsenko and Gait, 2000, *J. Org. Chem.* 65(16): 4900.

The specificity of the *Staphylococcus aureus* detection method of this invention is unexpectedly high. When nucleic acid templates from *Staphylococcus aureus, E. coli, Salmonella* spp., *Shigella* spp., *Enterobacter aerogenes, Citrobacter freundii, Klebsiella pneumoniae, Listeria monocytogenes, Vibrio parahaemolyticus, Bacillus cereus*, and *Streptococcus agalactiae* are amplified with the selected primer pair Sta27 and Sta28 or primer pair Sta29 and Sta30, only *Staphylococcus aureus* template can be amplified, and there is no amplification of templates prepared from other bacteria (see Example 1 below). Most unexpected is the ability of the two primer pairs to discriminate a *Staphylococcus aureus* template from templates prepared from other *Staphylococcus* species (e.g., *hominis, cohnii, carnusus, lentus, warneri, simulans, xylosus, caprae, epidermidis, arlettae, intermedius, saprophyticus, haemolyticus*, and *capitis*; see Example 1 below).

The sensitivity of the *Staphylococcus aureus* detection method of this invention is also unexpectedly high. Specifically, the amount of *Staphylococcus aureus* DNA that can be detected is as low as equivalent to an extract from 1 ml of a $10^2$ cfu/ml culture with primer pair Sta27/Sta28 and equivalent to an extract from 1 ml of a $10^4$ cfu/ml culture with primer pair Sta29/Sta30 (see Example 2 below).

Also within the scope of this invention is use of *Staphylococcus aureus*-specific sequences described above in combination with other species-specific nucleic acid sequences for simultaneously identification of multiple microorganisms.

Furthermore, at positions where single nucleotide polymorphisms occur, nucleotide variations are allowed in primers and probes described in this invention. As single nucleotide polymorphisms may be associated with a particular genotype or phenotype, these primers and probes can be used to distinguish and categorize different *Staphylococcus aureus* strains.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE 1

Detection of *Staphylococcus aureus* Using Specific Oligo-nucleotide Primers (1) Bacterial Strains Four groups of bacterial strains were used in this example (see TABLE 1 below):

(a) *Staphylococcus* group, including 15 *Staphylococcus* spp. (*aureus, hominis, cohnii, carnusus, lentus, warneri, simulans, xylosus, caprae, epidermidis, arlettae, intermedius, saprophyticus, haemolyticus*, and *capitis*);

(b) *E. coli* group, including 64 strains (8 non-pathogenic and 56 pathogenic subtypes/serotypes);

(c) *Salmonella* group, including 56 *Salmonella* spp.; and (d) Other bacteria group, including 11 pathogenic strains (4 *Shigella* spp.; 3 coliform bacteria *Enterobacter aerogenes, Citrobacter freundii*, and *Klebsiella pneumoniae*; 3 other food-borne pathogenic bacterial strains *Listeria monocytogenes, Vibrio parahaemolyticus*, and *Bacillus cereus*; and 1 infectious bacterial strain causing cattle mastitis, *Streptococcus agalactiae*).

These bacterial strains were obtained from different sources, such as Culture Collection and Research Center (CCRC; Hsin-Chu, Taiwan), National Laboratory for Food and Drugs (NLFD; Taipei, Taiwan, R.O.C.), American Type Culture Collection (ATCC; Rockville, Md., USA), United States Department of Agriculture (USDA; Washington, D.C., USA), Center of Vaccine Development (CVD; University of Maryland, Baltimore, Md., USA), and Pingtung University of Technology (PT; Pingtung, Taiwan, R.O.C.).

(2) Bacterial Culture

Cultivation of individual bacterial strains. One loopful of each test strain was plated on Luria-Bertani agar (LB; 0.5% yeast extract, 1% trypton, 0.5% NaCl, 1.5–2% agar), and was incubated for overnight (14 hr) at 37° C. A single colony was picked and inoculated into 3 ml

TABLE 1

Bacterial strains

| Strain | No. of Strains | Strain Name and Source |
|---|---|---|
| (a) *Staphylococcus* group | 15 | |
| *Staphylococcus* spp. | 15 | FP1-1 (*aureus*, CCRC10780), FP2-2 (*hominis*, CCRC12156), FP2-3 (*cohni* subtyp. *cohni*, CCRC12155), FP2-4 (*carnusus*, CCRC12922), FP2-5 (*lentus*, CCRC12926), FP2-6 (*warneri*, CCRC12929), FP2-7 (*simulans*, CCRC10778), FP2-8 (*xylosus*, CCRC12930), FP2-9 (*caprae*, CCRC13911), FP2-10 (*epidermidis*, CCRC10783), FP2-11 (*arlettae*, CCRC13975), FP2-12 (*intermedius*, CCRC12517), FP2-13 (*saprophyticus*, CCRC10786), FP2-14 (*haemolyticus*, CCRC12923), FP2-15 (*capitis*, CCRC12161) |

TABLE 1-continued

Bacterial strains

| Strain | No. of Strains | Strain Name and Source |
|---|---|---|
| (b) E. coli group | 64 | |
| Non-pathogenic E.coli | 8 | FP2-27 (CCRC11509), FP3-27, FP3-28 (ATCC25922), FP3-29 (ATCC11775), FP3-30, FP3-31, FP3-32, FP3-33 |
| Enteroaggregative E. coli (EAggEC) | 5 | FP2-32 (TVGH), FP2-33 (CVD), FP2-34 (CVD, O86:H2), FP2-35 (TVGH2), FP2-36 (TVGH) |
| Enteroinvasive E. coli (EIEC) | 2 | FP1-39 (O124:NM, CCRC15375), FP2-31 (O164:H, CVD) |
| Enterohemoehagic E. coli (EHEC) | 37 | FP1-37 (CCRC14825), FP1-40 (CCRC15373), FP1-41 (CCRC14824), FP1-42 (CCRC13089), FP3-9 (CCRC14815), FP3-10 (CCRC13084), FP3-11 (CCRC13086), FP3-12 (CCRC35150), FP3-13 (CCRC43890), FP3-14 (CCRC13093), FF3-15 (CCRC13094), FP3-16 (CCRC13095), FP3-17 (CCRC13096), FP3-18 (CCRC13097), FP3-19 (CCRC13098), FF3-20 (CCRC13099), FP2-45 (NLFD I20), FP2-46 (NLFD I61), FF2-47 (NQS317), FP2-48 (USDA014-90), FP2-49 (USDA115-93), FP2-50 (USDA028-00), FP3-1 (USDA177-93), FP3-2 (USDA042-91), FP3-3 (USDA037-90), FP3-4 (USDA45750), FP3-5 (USDA45753), FP3-6 (USDA45756), FF3-7 (USDA54a-7), FP3-8 (USDAAMF1847), FP3-9 (USDA008-90), FP3-26 (USDA012-89), FP3-21, FP3-22, FP3-23, FP3-24, FP3-25, FP3-25 (USDA008-90) |
| Enteropathogenic E. coli (EPEC) | 5 | FP1-35 (CCRC15530), FP1-36 (CCRC15536), FP2-38 (CVD), FP2-39 (CVD), FP2-40 (NQS) |
| Enterotoxigenic E. coli (ETEC) | 7 | FP1-38 (CCRC15372), FP2-25 (CCRC15370), FP2-26 (CCRC15371), FP2-41 (CCRC41443), FP2-42 (WHO103), FP2-43 (WHO110), FP2-44 (WHO112) |
| (c) Salmonella group | 56 | |
| Salmonella spp. | 56 | FP1-23 (typhi, CCRC14875), FP1-24 (typhimurium, CCRC10747), FP1-25 (salamae, CCRC15450), FP1-26 (typhimurium, CCRC10248), FP1-27 (paratyphiA, CCRC14878), FP1-28 (typhimurium, CCRC12947), FP1-29 (california, CCRC15454), FP1-30 (enteritidis), FP1-31 (typhi, CCRC 10746), FP1-32 (paratyphi B, CCRC14897), FP1-33 (etterbeele, CCRC15455), FP1-34 (postsdam, CCRC15433), FP3-34 (aberdeen, US), FP3-35 (adelaide, US), FP3-36 (albany, USDA), FP3-37 (amager, US), FP3-38 (anatum, PT), FP3-39 (bareilly, USDA), FP3-40 (berta, US), FP3-41 (california, US), FP3-42 (cerro, USDA671D), FP3-43 (cerro, USDA), FP3-44 (chester, USDA), FP3-45 (coleypark, US), FP3-46 (crossness, US), FP3-47 (cubana, USDA), FP3-48 (djakarta, US ), FP3-49 (drypool, USDA607E), FP3-50 (dublin, US), FP4-1 (dugbe, US), FP4-2 (enteritidis, ATCC13076), FP4-3 (enteritidis, US), FP4-4 (emek, US), FP4-5 (eppendorf, PT633), FP4-6 (florida, US), FP4-7 (hartford, USDA), FP4-8 (havana, US), FP4-9 (hvttingfoss, USDA), FP4-10 (hvttingfoss, US), FP4-11 (infantis, US), FP4-12 (java, US), FP4-13 (kentuky, US), FP4-14 (litchfield, US), FP4-15 (london, PT1004), FP4-16 (miami, US), FP4-17 (munster, PT1014), FP4-18 (newbrunswick, US), FP4-19 (newington, USDA), FP4-20 (newington, USDA), FP4-21 (newport, US), FP4-22 (ohio, PT1007), FP4-23 (panama, US), FP4-24 (pomona, USDA), FP4-25 (Poona, USDA), FP4-26 (taksony, USDA1121D), FP4-27 (thomasville, USDA1101E) |
| (d) Other bacteria group | 11 | |
| Shigella spp. | 4 | FP2-18 (dysenteria, CCRC13983), FP2-19 (boydii, CCRC15961), FP2-20 (flexneri, CCRC10772), FP2-21 (sonnei, CCRC10773) |
| Coliform bacteria | 3 | FP2-29 (Enterobacter aerogenes, CCRC10370), FP2-28 (Citrobacter freundii, CCRC 12291), FP2-30 (Klebsiella pneumoniae, CCRC 15627) |
| Food-borne pathogenic bacteria | 3 | FP2-24 (Listeria monocytogenes, CCRC14930), FP2-22 (Vibrio parahaemolyticus, CCRC10806), FP2-16 (Bacillus cereus, CCRC11827) |
| Streptococcus agalactiae | 1 | FP1-43 (Streptococcus agalactiae, CCRC10787) | sterilized LB broth, and was incubated for overnight at 37° C. with shaking at 150–180 rpm. The density of each bacterial culture was ~$1 \times 10^{10}$ cells/ml.

Preparation of bacterial mixtures. For the Staphylococcus group, a mixture was prepared by combining all 15 overnight cultures (0.05 ml each). For the E. coli group and the Salmonella group, a "pre-mix" was prepared by combining overnight cultures of every 10 bacterial strains (0.05 ml each) in the same group. The last pre-mix in the E. coli group has 14 strains, and the last pre-mix in the Salmonella group has 6 strains. A "final mix" was then prepared by combining one hundred microliters of each pre-mix. For the other bacteria group, a mixture was prepared by combining all 11 overnight cultures (0.05 ml each).

(3) Preparation of Bacterial Genomic DNA

Genomic DNA was isolated from bacterial mixtures by using MicroLYSIS™ (Microzone Limited, UK). 17 μl MicroLYSIS™ buffer was mixed with three microliters of each bacterial culture mix. Genomic DNA was extracted according to the manufacturer's protocol with the suggested thermal cycling profile: step 1—65° C. for 5 min, step 2—96° C. for 2 min, step 3— 65° C. for 4 min, step 4—96° C. for 1 min, step 5—65° C. for 1 min, step 6—96° C. for 30 sec, and step 7—hold at 20° C. The MicroLYSIS™/DNA mixture after thermal cycling treatment was directly applied as a DNA template for amplification. Theoretically, 1 μl of such MicroLYSIS™/DNA mixture contained genomic DNA extracted from $1.8 \times 10^4$–$1.4 \times 10^5$ cells of each bacterial strain.

(4) Amplification of Bacterial Genomic DNA with Staphylococcus aureus-Specific Oligo-Nucleotide Primers Amplification mixture. Fifty microliters of amplification reaction mixture contains 5 μl 10×Taq DNA polymerase buffer (Promega, Madison, Wis., USA), 5 µl 25 mM MgCl₂ (Promega), 5 µl 2.5 mM dNTPs (Promega), 1 µl of each oligo-nucleotide primer (20 µM), 1 µl of total genomic DNA template as described above, 1 U of Taq DNA polymerase (Promega), and sterilized dH₂O.

Amplification conditions. Amplification was carried out using GeneAmp® PCR System 2400 (Perkin-Elmer) as follows: 95° C. for 2 min; 30 cycles of 95° C. for 30 sec, 55° C. for 30 sec, and 72° C. for 30 sec; and a final extension at 72° C. for 6 min.

(5) Analysis of Amplification Products by Agarose Electrophoreis

Amplified products (50 µl) were analyzed by electrophoresis on a 2% agarose gel in TAE buffer (40 mM Tris, 20 mM sodium acetate, 2 mM EDTA, pH adjusted with glacial acetic acid) and stained with ethidium bromide.

The experimental results show that the selected oligo-nucleotide primers are unexpectedly highly specific for detecting *Staphylococcus aureus*. When bacterial strains were tested in groups, i.e., groups (a)–(d), the predicted amplification products (molecular weight of 250 bp for primer pair Sta27/Sta28 and 300 bp for primer pair Sta29/Sta30) could only be detected in the *Staphylococcus* group. No amplification products were observed in the other 3 groups. Moreover, when the 15 *Staphylococcus* strains were individually tested, the predicted amplification products could only be detected with *Staphylococcus aureus*. No amplification products were observed for the other 14 *Staphylococcus* strains.

EXAMPLE 2

Detection Sensitivity of *Staphylococcus aureus*-specific Oligo-nucleotide Primers An overnight culture of *Staphylococcus aureus* was grown in LB broth at 37° C., and the cell concentration, colony forming unit/ml (cfu/ml), was determined. Genomic DNA was extracted from 1 ml of a $10^9$ cfu/ml culture, and was serially diluted to concentrations equivalent to extracts from 1 ml of $10^0$–$10^7$ cfu/ml cultures.

Amplification was carried out as described in Example 1, except that serial dilutions of *Staphylococcus aureus* genomic DNA were used as the templates. Unexpectedly, the amount of *Staphylococcus aureus* DNA that could be detected was as low as equivalent to an extract from 1 ml of a $10^2$ cfu/ml culture with primer pair Sta27/Sta28 and equivalent to an extract from 1 ml of a $10^4$ cfu/ml culture with primer pair Sta29/Sta30.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A pair of amplification primers, each containing an oligo-nucleotide selected from SEQ ID NO: 1, wherein each primer is shorter than 40 nucleotides in length, and the pair of primers participate in a polymerase chain reaction, with a *Staphylococcus aureus* nucleic acid as a template, to generate a nucleic acid that specifically hybridizes to SEQ ID NO: 1, wherein the oligo-nucleotides in the pair of primers contains. respectively, SEQ ID NOs:3 and 4 or SEQ ID NOs:5 and 6.

2. The pair of primers of claim 1, wherein each primer is shorter than 30 nucleotides in length.

3. The pair of primers of claim 1, wherein the oligo-nucleotides in the pair of primers are respectively, SEQ ID NOs:3 and 4.

4. The pair of primers of claim 1, wherein the oligo-nucleotides in the pair of primers are, respectively, SEQ ID NOs:5 and 6.

5. A method of detecting *Staphylococcus aureus*, the method comprising:

providing a sample having a nucleic acid from an unknown microorganism;

amplifying the nucleic acid with a pair of primers, as recited in claim 1, and detecting an amplification product;

whereby detection of the amplification product indicates the presence of *Staphylococcus aureus*.

6. The method of claim 5, wherein each is shorter than 30 nucleotides in length.

7. The method of claim 5, wherein the oligo-nucleotides are, respectively, SEQ ID NOs:3 and 4, or SEQ ID NOs:5 and 6.

8. The method of claim 5, wherein the detecting step includes hybridizing the amplification product to a nucleic acid probe that has 10–1000 nucleotides in length and contains an oligo-nucleotide selected from SEQ ID NO:1.

9. The method of claim 8, wherein the nucleic acid probe has 10–500 nucleotides in length.

10. The method of claim 9, wherein the nucleic acid probe has 10–250 nucleotides in length.

11. The method of ciaim 10, wherein the nucleic acid probe has 10–50 nucleotides in length.

12. The method of claim 8, wherein the oligo-nucieotide is selected from SEQ ID NO:2 or a sequence complementary thereto.

13. The method of claim 12, wherein the oligo-nucleotide is SEQ ID NO:2 or a sequence complementary thereto.

14. The method of claim 8, wherein the oligo-nucleotide is selected from SEQ ID NO:7, from SEQ ID NO: 8, or from a sequence complementary thereto.

15. The method of claim 14, wherein the oligo-nucleotide is SEQ ID NO:7, SEQ ID NO:8 , or a sequence complementary thereto.

* * * * *